United States Patent
Mitsuda et al.

(10) Patent No.: US 8,026,396 B2
(45) Date of Patent: Sep. 27, 2011

(54) PROCESSES FOR THE PREPARATION OF OPTICALLY ACTIVE INTERMEDIATES

(75) Inventors: Masaru Mitsuda, Osaka (JP); Tadashi Moroshima, Osaka (JP); Kentaro Tsukuya, Osaka (JP); Kazuhiko Watabe, Osaka (JP); Masahiko Yamada, Osaka (JP)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 12/854,215

(22) Filed: Aug. 11, 2010

(65) Prior Publication Data

US 2010/0331575 A1    Dec. 30, 2010

Related U.S. Application Data

(63) Continuation of application No. 11/833,266, filed on Aug. 3, 2007, now Pat. No. 7,790,927.

(30) Foreign Application Priority Data

Aug. 5, 2006 (GB) .................................. 0615620.2

(51) Int. Cl.
    C07C 233/58 (2006.01)
(52) U.S. Cl. ........................................ 564/161; 564/190
(58) Field of Classification Search .................. None
    See application file for complete search history.

(56) References Cited

U.S. PATENT DOCUMENTS

| 4,411,925 | A  | 10/1983 | Brennan et al. |
| 4,590,292 | A  | 5/1986  | Blackwell et al. |
| 4,933,477 | A  | 6/1990  | Goetz et al. |
| 5,225,602 | A  | 7/1993  | Hoelderich et al. |
| 5,728,873 | A  | 3/1998  | Kleemiss et al. |
| 6,552,217 | B2 | 4/2003  | Hubbs et al. |
| 6,683,216 | B1 | 1/2004  | Zoeller et al. |
| 7,790,927 | B2 * | 9/2010 | Mitsuda et al. ............... 564/307 |

FOREIGN PATENT DOCUMENTS

| DE | 3909142  | 10/1990 |
| DE | 4315623  | 11/1994 |
| DE | 19523868 | 1/1997  |
| EP | 0205403  | 12/1986 |
| EP | 0393350  | 10/1990 |
| EP | 1418168  | 5/2004  |
| WO | 0192263  | 12/2001 |

OTHER PUBLICATIONS

Office Action dated Dec. 30, 2009 received in copending U.S. Appl. No. 11/833,263.
Tomoskozi, Tetrahedron (1963) 19(12):1969-1979 Abstract.
Office Action dated Apr. 23, 2009 received in copending U.S. Appl. No. 11/833,263.
Engel et al., "Photochemistry of azocyclopropane," J Org Chem (1988) 53(20):4748-4758.
Database CAPLUS on STN, Acc. No. 1971:435269, Filler et al., J. Chem. Soc., Section C: Organic (1971), 11, p. 2062-2068 (abstract).
Yasuri et al., "Vibrational circular dichroism of optically active cyclopropanes. 3. trans-2-Phenylcyclopropanecarboxylic acid derivatives and related compounds," J Am Chem Soc (1987) 109(8):2311-2320.
Armstrong et al., "Stereocontrolled synthesis of 3-(trans-2-aminocyclopropyl)alanine, a key component of belactosin A," Organic Letters (2003) 5(13):2331-2334.
Barbieri et al., "Chemo-enzymatic synthesis of (R)- and (S)-3,4-dichlorophenylbutanolide intermediate in the synthesis of sertraline," Tetrahedron: Asymmetry (1999) 10:3931-3937.
Wang et al., "Enantioselective synthesis of chiral cyclopropane compounds through microbial transformations of trans-2-arylcyclopropanecarbonitriles," Tetrahedron Letters (2000) 41:6501-6505.
White "New reactions of polyfluoroaromatic compounds. Part II. Polyfluoroaralkyl amines," J. Chem Soc. (1971) 2062-2068.
Singh et al., "Development of a practical, safe, and high-yielding process for the preparation of enatiomerically pure trans-cyclopropane carboxylic acid," Organic Process Research & Development (2002) 6:618-620.
Notice of Allowance dated Sep. 7, 2010 received in copending U.S. Appl. No. 11/833,263.

* cited by examiner

*Primary Examiner* — Brian J Davis
(74) *Attorney, Agent, or Firm* — Pepper Hamilton LLP

(57) ABSTRACT

This invention relates to processes for the production of optically active 2-(disubstituted aryl)cyclopropylamine compounds and optically active 2-(disubstituted aryl)cyclopropane carboxamide compounds which are useful intermediates for the preparation of pharmaceutical agents, and in particular the compound [1S-(1α,2α,3β(1S*,2R*),5β)]-3-[7-[2-(3,4-difluorophenyl)-cyclopropyl]amino]-5-(propylthio)-3H-1,2,3-triazolo[4,5-d]pyrimidin-3-yl)-5-(2-hydroxyethoxy)-cyclopentane-1,2-diol.

2 Claims, No Drawings

PROCESSES FOR THE PREPARATION OF OPTICALLY ACTIVE INTERMEDIATES

CROSS-REFERENCE TO RELATED APPLICATIONS

This application is a continuation of U.S. Ser. No. 11/833,266 filed Aug. 3, 2007, which claims priority to Great Britain Application No. 0615620.2 filed Aug. 5, 2006, each of which is incorporated herein by reference in its entirety.

FIELD OF THE INVENTION

This invention relates to processes for the production of optically active 2-(disubstituted aryl)cyclopropylamine derivatives and optically active 2-(disubstituted aryl)cyclopropane carboxamide derivative which are useful intermediates for the preparation of pharmaceutical agents, and in particular the compound [1S-(1α,2α,3β(1S*,2R*),5β)]-3-[7-[2-(3,4-difluorophenyl)-cyclopropyl]amino]-5-(propylthio)-3H-1,2,3-triazolo[4,5-d]pyrimidin-3-yl)-5-(2-hydroxyethoxy)-cyclopentane-1,2-diol. This compound, and similar such compounds, are disclosed in WO 00/34283 and WO 99/05143. These compounds are disclosed as $P_{2T}$ (which is now usually referred to as $P_2Y_{12}$) receptor antagonists. Such antagonists can be used as, inter alia, inhibitors of platelet activation, aggregation or degranulation.

BACKGROUND OF THE INVENTION

Some processes are known for the production of optically active 2-cyclopropane carboxamide derivatives, optically active 2-aryl cyclopropylamine derivatives, and optically active 2-arylcyclopropane-1-carboxylate ester derivatives.

Examples of processes for the production of optically active 2-arylcyclopropane carboxamide derivatives are:

(i) A process wherein excess thionyl chloride is reacted with optically active 2-phenylcyclopropane carboxylic acid in benzene solvent to form corresponding acid chloride, and after concentrating down excess thionyl chloride and benzene under reduced pressure, the acid chloride is isolated and purified by distillation, and, by causing ammonia water to act on this, 2-phenylcyclopropane carboxamide is obtained (J. Am. Chem. Soc. Vol. 109, p. 2311 (1987), Journal of Medicinal Chemistry Vol. 20, p. 771 (1977)); and (ii) A Process to obtain optically active 3-aryl-2-dimethylcyclopropane-1-carboxamide by causing ammonia water to act on the corresponding acid chloride formed by reacting thionyl chloride with optically active 3-aryl-2-dimethylcyclopropane-1-carboxylic acid (J. Org. Chem. Vol. 68, p. 621 (2003)).

Examples of processes for the production of optically active 2-aryl cyclopropylamine derivatives are:

(iii) A process wherein chlorocarbonic acid ethyl ester is reacted with 2-aryl cyclopropane carboxylic acid to form mixed acid anhydride, and by causing to act sodium azide on this, corresponding acid azide is formed, and 2-aryl cyclopropylamine is obtained by Curtius rearrangement with this (Journal of Medicinal Chemistry Vol. 20, p. 771 (1977), WO01/92263); and (iv) A process to obtain corresponding 2,2-dimethyl cyclopropylamine by causing chlorine, bromine or sodium hypochlorite to act on the optically active 2,2-dimethylcyclopropane-1-carboxamide in the presence of base (Kokoku 5-3865);

Examples of a process for the production of optically active 2-arylcyclopropane carboxylate ester derivatives are:

(v) A process to obtain optically active cyclopropanecarboxylic acid derivative by cyclopropanation after deriving into optically active ester or amide via several steps using benzaldehyde derivative as the starting material (WO01/92263); and (vi) A process to obtain optically active 2-dihydrofuranyl cyclopropanecarboxylate derivative by reacting phosphonoacetic acid ester derivative with optically active dihydrobenzofuranyl ethylene oxide derivative in the presence of base (Organic Process Research & Development, vol 6, p. 618 (2002)).

Examples of a process to produce optically active 2-aryl cyclopropylamine derivatives from optically active 2-aryl cyclopropanecarboxylic acid are:

(vii) A process wherein benzaldehydes is used as the starting material and derived into optically active ester or amide via several steps, and thereafter optically active 2-aryl cyclopropane carboxylate ester is obtained by cyclopropanation. This optically active carboxylic acid derivative is formed into acid azide, and optically active 2-aryl cyclopropylamine derivative is produced by Curtius rearrangement (WO01/92263).

In the process for the production of optically active 2-arylcyclopropane carboxamides referred to in (i) above, only the process to produce 2-phenylcyclopropane carboxamide from 2-phenylcyclopropane carboxylic acid is described and a process for production for 2-(disubstituted aryl)cyclopropane carboxamide derivative is not disclosed. Moreover, in the process (ii) above, there is mentioned the process for production only of 2,2-dimethyl-3-phenylcyclopropane carboxamide and 2,2-dimethyl-3-isopropylidene cyclopropane carboxamide, and a process for production of 2-(disubstituted aryl)cyclopropane carboxamide derivative is not disclosed.

Secondly, in a process for the production of optically active 2-aryl cyclopropylamine derivative, optically active 2-aryl cyclopropylamine derivative is produced by Curtius rearrangement from optically active 2-arylcyclopropane carboxylic acid in the aforesaid process (iii), however, it is not suitable for a commercial preparation method from the viewpoint of safety because it is via an acid azide intermediate having explosive properties. Moreover, in the process (iv), optically active amine is produced from the optically active carboxamide by a Hofmann rearrangement. However, it is not suitable for a commercial preparation method from the viewpoint of economy because yield is low when the reaction is carried out using the sodium hypochlorite. Moreover, as for the aforesaid process (iv), only the process to produce optically active 2,2-dimethyl cyclopropylamine from optically active 2,2-dimethylcyclopropane carboxamide is mentioned, and a process for production of 2-(disubstituted aryl)cyclopropane carboxamide derivative is not disclosed.

Thirdly, in a process for the production of optically active 2-arylcyclopropane carboxylate ester derivative, in the aforesaid process (v), optically active 3,4-difluorophenyl cyclopropanecarboxylic derivative is obtained by cyclopropanation after converting 3,4-difluoro benzaldehyde starting material into optically active ester or amide via several steps. However, it is not commercially suitable from the viewpoint of productivity and economy. For example, the starting material is expensive, the stereoselectivity is insufficient in the cyclopropanation and also there are many numbers of steps. Moreover, in process (vi), only an example of preparing optically active dihydrofuranyl cyclopropanecarboxylate ester from optically active dihydrobenzofuranyl ethylene oxide is mentioned. It is not a process for the production of general optical activity 2-arylcyclopropane carboxylate ester.

Fourthly, a process to produce optically active 2-aryl cyclopropylamine derivative from optically active 2-arylcyclopropane carboxylate ester derivative using (vii) is not commercially viable from a safety standpoint because the acid azide intermediate has expulsion properties. Also, purification is essential due to insufficient stereoselectivity during the cyclopropanation, making this process unsuitable for commercial preparation because of poor productivity.

Thus, the processes outlined are unsuitable for commercial production. There is a need for a commercial process which addresses areas such as safety, economy, productivity and the like.

SUMMARY OF THE INVENTION

The present invention provides processes for the production of an optically active cyclopropylamine compound represented by general formula (2), or a salt thereof,

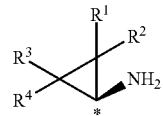
(2)

wherein each of $R^1$, $R^2$, $R^3$, and $R^4$ is, independently, selected from a hydrogen atom, optionally substituted $C_{1-10}$ cyclic or acyclic alkyl group, optionally substituted $C_{6-10}$ aryl group or optionally substituted $C_{7-10}$ aralkyl group, and wherein * denotes an asymmetric carbon centre; characterised by the reaction of an optically active cyclopropane carboxamide compound represented by general formula (1)

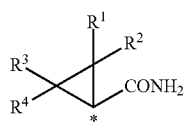
(1)

wherein each of $R^1$, $R^2$, $R^3$, $R^4$ and * are the same as for the cyclopropylamine compound represented by general formula (2)) with hypochlorite in water in the presence of 5-30 equivalents of alkali metal hydroxide.

The present invention also provides processes for the production of an optically active 2-aryl cyclopropylamine compound represented by general formula (9), or a salt thereof,

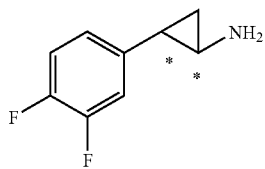
(9)

wherein * denotes an asymmetric carbon centre, and wherein an optically active 2-aryl cyclopropanecarboxylic acid compound represented by general formula (7), wherein * denotes an asymmetric carbon centre, is obtained,

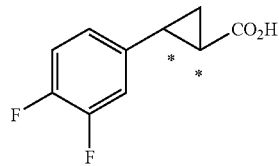
(7)

by de-esterifying an optically active 2-arylcyclopropane carboxylate ester compound represented by general formula (6)

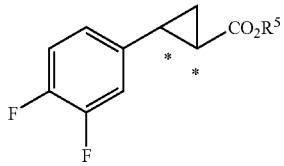
(6)

wherein $R^5$ is an optionally substituted $C_{1-10}$ cyclic or acyclic alkyl group, optionally substituted $C_{6-10}$ aryl group, or optionally substituted $C_{7-10}$ aralkyl group, and * denotes an asymmetric carbon centre, and wherein the compound of formula (6) is obtained by reacting an optically active styrene oxide compound represented by general formula (3)

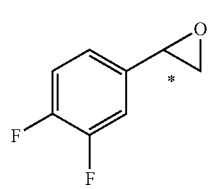
(3)

wherein * denotes an asymmetric carbon centre, or optically active halohydrin compound represented by general formula (4)

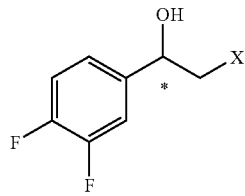
(4)

wherein X denotes a halogen atom, and * denotes an asymmetric carbon centre, with a phosphonoacetic acid ester compound represented by general formula (5)

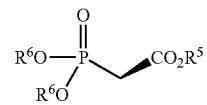
(5)

wherein each $R^5$ and $R^6$ is, independently, a substituted $C_{1-10}$ cyclic or acyclic alkyl group, optionally substituted $C_{6-10}$ aryl group, or optionally substituted $C_{7-10}$ aralkyl group, in the presence of base; and thereafter, the 2-aryl cyclopropanecarboxylic acid compound of formula (7) obtained is activated by reaction with a carboxylic acid activator and thereafter reacting with ammonia to give the optically active 2-aryl cyclopropane carboxamide compound represented by obtained general formula (8)

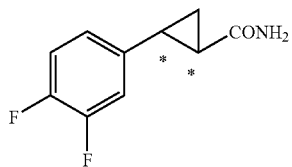

(8)

wherein * denotes an asymmetric carbon centre, which is reacted with an oxidant to give the compound of formula (9).

The present invention also provides processes for the production of optically active 2-aryl cyclopropane carboxamide compound represented by general formula (12)

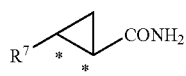

(12)

wherein $R^7$ is an aryl group substituted by 2 or more halogen atoms, and * denotes an asymmetric carbon centre, characterized in that, an optically active 2-aryl cyclopropanecarboxylic acid compound represented by general formula (10)

(10)

wherein $R^7$ is an aryl group substituted by 2 or more halogen atoms, and * denotes an asymmetric carbon centre, is reacted with a carboxylic acid activator with the formation of an optically active 2-aryl cyclopropanecarboxylic acid compound represented by general formula (11)

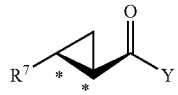

(11)

wherein $R^7$ is an aryl group substituted by 2 or more halogen atoms, Y is a carbonyl group activated group, and * denotes an asymmetric carbon centre, and thereafter this optically active 2-aryl cyclopropanecarboxylic acid compound represented by general formula (11) is reacted with ammonia.

The present invention also provides optically active 2-aryl cyclopropane carboxamide compounds represented by general formula (17)

(17)

wherein, $R^{10}$ is an aryl group substituted by 2 or more halogen atoms, and * denotes an asymmetric carbon centre.

DESCRIPTION OF EMBODIMENTS

Efficient processes have now been discovered for the production of optically active 2-aryl cyclopropylamine derivatives or salts thereof. The processes afford high optical purity by using a readily available optically active styrene oxide derivative as the starting material. Efficient processes for the production of optically active cyclopropylamine derivative by a Hofmann rearrangement using sodium hypochlorite have been discovered. These processes can be used safely and inexpensively as commercial preparation methods.

Thus, according to the present invention there is provided a process for the production of optically active cyclopropylamine derivatives (or compounds) represented by general formula (2) or salts thereof

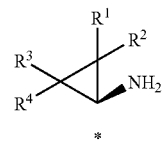

(2)

(wherein $R^1$, $R^2$, $R^3$ or $R^4$ denote a hydrogen atom, optionally substituted $C_{1-10}$ cyclic or acyclic alkyl group, optionally substituted $C_{6-10}$ aryl group, or optionally substituted $C_{7-10}$ aralkyl group, and * denotes an asymmetric carbon centre), characterised by reacting optically active cyclopropane carboxamide derivative (or compound) represented by general formula (1)

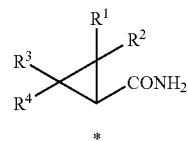

(1)

(wherein $R^1$, $R^2$, $R^3$, $R^4$ and * have the same said definitions) with hypochlorite in water in the presence of alkali metal hydroxide of 5-30 equivalent.

Suitably, the hypochlorite is sodium hypochlorite; and in particular the quantity used of the hypochlorite is 1-5 mole equivalent with respect to compound of the formula (1). In a particular embodiment, there is provided a process for the production of optically active cyclopropylamine derivatives or salts thereof wherein $R^1$, $R^2$, $R^3$ is hydrogen atom and $R^4$ is 3,4-difluorophenyl group.

In a further embodiment, there is provided is a process for the production of an optically active 2-aryl cyclopropylamine derivative (or compound) represented by general formula (9) or a salt thereof, (9)

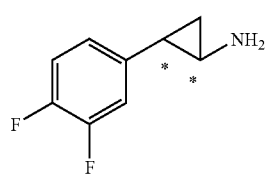

(wherein * denotes an asymmetric carbon centre), wherein an optically active 2-aryl cyclopropanecarboxylic acid derivative (or compound) represented by general formula (7)

(7)

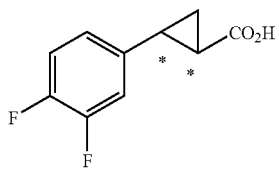

(wherein * denotes an asymmetric carbon centre) is obtained by de-esterifying the optically active 2-arylcyclopropane carboxylate ester derivative (or compound) represented by general formula (6)

(6)

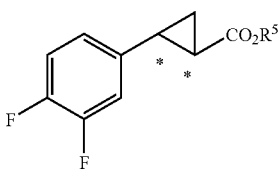

(wherein, $R^5$ denotes optionally substituted $C_{1-10}$ cyclic or acyclic alkyl group, optionally substituted $C_{6-10}$ aryl group, or optionally substituted $C_{7-10}$ aralkyl group, and * denotes an asymmetric carbon centre) which is obtained by reacting the optically active styrene oxide derivative (or compound) represented by general formula (3)

(3)

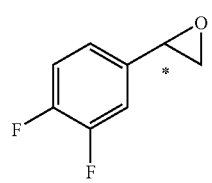

(wherein * denotes an asymmetric carbon centre) or optically active halohydrin derivative (or compound) represented by or general formula (4)

(4)

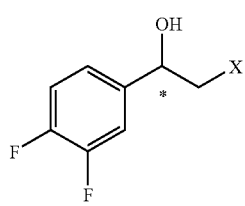

(wherein X denotes a halogen atom, and * denotes an asymmetric carbon centre) with phosphonoacetic acid ester derivative (or compound) represented by general formula (5)

(5)

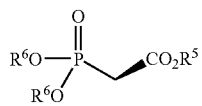

(wherein $R^5$ or $R^6$ denote optionally substituted $C_{1-10}$ cyclic or acyclic alkyl group, optionally substituted $C_{6-10}$ aryl group or optionally substituted $C_{7-10}$ aralkyl group) in the presence of base, and optically active 2-aryl cyclopropane carboxamide derivative (or compound) represented by obtained general formula (8)

(8)

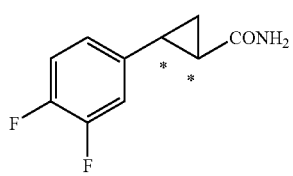

(wherein * denotes an asymmetric carbon centre) which is obtained by reacting the obtained aforesaid 2-aryl cyclopropanecarboxylic acid derivative (or compound) with ammonia after being activated with carboxylic acid activator is reacted with oxidant.

There is also provided a process for the production of optically an active 2-aryl cyclopropane carboxamide derivative (or compound) represented by general formula (12)

(12)

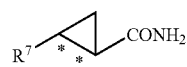

(wherein $R^7$ denotes an aryl group substituted by 2 or more halogen atoms, and * denotes an asymmetric carbon centre) characterized by reacting with ammonia, optically active 2-aryl cyclopropanecarboxylic acid derivative (or compound) represented by general formula (11)

(11)

(wherein, $R^7$ denotes an aryl group substituted by 2 or more halogen atoms, Y denotes carbonyl group activated group, and * denotes an asymmetric carbon centre) which is obtained from an optically active 2-aryl cyclopropanecarboxylic acid derivative (or compound) represented by general formula (10)

(10)

(wherein $R^7$ denotes an aryl group substituted by 2 or more halogen atoms, and * denotes an asymmetric carbon centre) by reacting with a carboxylic acid activator.

There is also provided a process for the production of an optically active 2-aryl cyclopropane carboxamide derivative (or compound), wherein the reaction is carried out by using the compound of formula (10) obtained by de-esterifying an optically active 2-aryl cyclopropane carboxylate ester derivative (or compound) represented by general formula (13)

(13)

(wherein R⁸ denotes optionally substituted $C_{1-10}$ cyclic or acyclic alkyl group, optionally substituted $C_{6-10}$ aryl group, or optionally substituted $C_{7-10}$ aralkyl group, and R⁷ and * have the same said definitions).

There is also provided a process for the production of an optically active 2-aryl cyclopropane carboxamide derivative (or compound), wherein the reaction is carried out by using the compound of formula (13) obtained by reacting the optically active styrene oxide derivative represented by general formula (14)

(14)

(wherein R⁷ and * have the same said definitions) or optically active halohydrin derivative (or compound) represented by general formula (15)

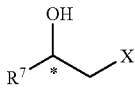

(15)

(wherein R⁷ and * have the same said definitions) with phosphonoacetic acid ester derivative (or compound) represented by general formula (16)

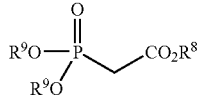

(16)

(wherein R⁹ denotes optionally substituted $C_{1-10}$ cyclic or acyclic alkyl group, optionally substituted $C_{6-10}$ aryl group, or optionally substituted $C_{7-10}$ aralkyl group, and R⁸ and * have the same said definitions) in the presence of base. There is also provided a process for the production of an optically active 2-aryl cyclopropane carboxamide derivative (or compound) to obtain (1R,2R)-2-aryl cyclopropane carboxamide derivative (or compound) of formula (12) using a (1R,2R)-2-aryl cyclopropanecarboxylic acid derivative (or compound) of formula (10). The present invention also provides a process for the production of an optically active 2-aryl cyclopropane carboxamide derivative (or compound) to obtain a (1R,2R)-2-aryl cyclopropane carboxylic acid derivative (or compound) formula (10) using a (1R,2R)-2-aryl cyclopropane carboxylate ester derivative (or compound) of formula (13).

There is also provided a process for the production of an optically active 2-aryl cyclopropane carboxamide derivative (or compound) to obtain a (1R,2R)-2-aryl cyclopropane carboxylate ester derivative (or compound) of formula (13) using (S)-styrene oxide derivative formula (14) and (S)-halohydrin derivative (or compound) of formula (15). In particular, there is provided a process for the production of an optically active 2-aryl cyclopropane carboxamide derivative (or compound), wherein R⁷ is 3,4-difluorophenyl group.

The present invention also provides an optically active 2-arylcyclopropane carboxamide derivative (or compound) represented by general formula (17)

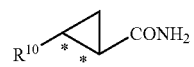

(17)

(wherein R¹⁰ denotes an aryl group substituted by 2 or more halogen atoms, and * denotes an asymmetric carbon centre).

In particular, in the optically active 2-arylcyclopropane carboxamide derivative (or compound) of formula (17), R¹⁰ is a 3,4-difluorophenyl group.

More particularly, the compound of formula (17) is a (1R, 2R)-2-aryl cyclopropane carboxamide derivative (or compound).

The present invention provides a process for preparing an optically active aminocyclopropane derivative (or compound) from inexpensive 3,4-difluorobenzene using a Hoffmann re-arrangement. In general, the process is a safe and inexpensive way of preparing the optically active aminocycloprane derivative which is useful as an intermediate in the manufacture of pharmaceuticals and pesticides.

The conversion of compounds of formula (14) to (2) comprises 4 steps, namely in total: 1) cyclopropanation process, 2) deesterification process, 3) amidation process and 4) Hofmann rearrangement process. Hereinafter, the invention is described in detail for each process.

Firstly, there will be described 1) cyclopropanation process.

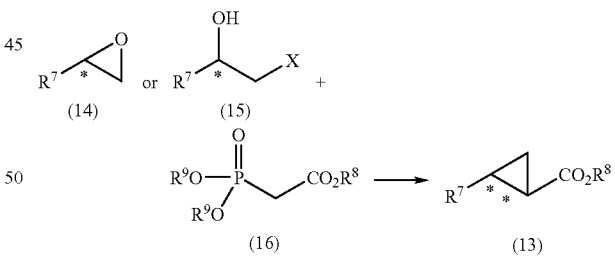

Step 1. Cyclopropanation Process

In compounds represented by formula (14), R⁷ denotes an aryl group substituted by 2 or more halogen atoms. Suitable values for R⁷ include, for example, a 2,3-difluorophenyl group, 3,4-difluorophenyl group, 2,4-difluorophenyl group, 2,3,4-trifluorophenyl group, 3,4,5-trifluorophenyl group, 2,3,4,5-tetrafluorophenyl group, 2,3,4,5,6-pentafluorophenyl group, 2,3-dichlorophenyl group, 3,4-dichlorophenyl group, 2,4-dichlorophenyl group, 2,3,4-trichlorophenyl group, 3,4,5-trichlorophenyl group, 2,3,4,5-tetrachlorophenyl group, 2,3,4,5,6-pentachlorophenyl group, 2,3-dibromophenyl group, 3,4-dibromophenyl group, 2,4-dibromophenyl group, 2,3,4-tribromophenyl group, 3,4,5-tribromophenyl group, 2,3,4,5-tetrabromophenyl group, and a 2,3,4,5,6-pentabromo phenyl group. A 3,4-difluorophenyl group is preferred. Moreover, * denotes an asymmetric carbon centre. In other words, a styrene oxide derivative formula (14) contains an asymmetric carbon centre. This invention includes any optically active substance or racemic mixture of the compound of formula (14). Preferably, it is optically active substance, and most preferably it is a compound whose absolute configuration of asymmetric carbon centre is (S).

In the compound of formula (15), $R^7$ denotes an aryl group substituted by 2 or more halogen atoms, and X denotes a halogen atom. Suitable values for $R^7$ include, for example, a 2,3-difluorophenyl group, 3,4-difluorophenyl group, 2,4-difluorophenyl group, 2,3,4-trifluorophenyl group, 3,4,5-trifluorophenyl group, 2,3,4,5-tetrafluorophenyl group, 2,3,4,5,6-pentafluorophenyl group, 2,3-dichlorophenyl group, 3,4-dichlorophenyl group, 2,4-dichlorophenyl group, 2,3,4-trichlorophenyl group, 3,4,5-trichlorophenyl group, 2,3,4,5-tetrachlorophenyl group, 2,3,4,5,6-pentachlorophenyl group, 2,3-dibromophenyl group, 3,4-dibromophenyl group, 2,4-dibromophenyl group, 2,3,4-tribromophenyl group, 3,4,5-tribromophenyl group, 2,3,4,5-tetrabromophenyl group, and a 2,3,4,5,6-pentabromo phenyl group. A 3,4-difluorophenyl group is preferred.

Moreover, * denotes an asymmetric carbon centre. In other words, the halohydrin derivative represented by general formula (15) contains asymmetric carbon centre. The invention includes any optically active substance or racemic mixture of the compound of formula (15). Preferably it is optically active substance, and most preferably it is a compound whose absolute configuration of asymmetric carbon centre is (S).

In the compound of formula (16), $R^8$ denotes an optionally substituted $C_{1-10}$ cyclic or acyclic alkyl group, optionally substituted $C_{6-10}$ aryl group, or optionally substituted $C_{7-10}$ aralkyl group, and $R^9$ denotes an optionally substituted $C_{1-10}$ cyclic or acyclic alkyl group, optionally substituted $C_{6-10}$ aryl group, or optionally substituted $C_{7-10}$ aralkyl group. Suitable values for a $C_{1-10}$ cyclic or acyclic alkyl group include for example, a methyl group, ethyl group, n-propyl group, i-propyl group, cyclopropyl group, n-butyl group, s-butyl group, i-butyl group, t-butyl group, cyclobutyl group, n-pentyl group, neopentyl group, cyclopentyl group, n-hexyl group, cyclohexyl group, n-heptyl group, cyclohexylmethyl group, n-octyl group, and n-decyl group. Suitable values for an optionally substituted $C_{6-10}$ aryl group include for example phenyl group, o-methoxyphenyl group, m-methoxyphenyl group, p-methoxy phenyl group, o-nitrophenyl group, m-nitrophenyl group, p-nitrophenyl group, o-chlorophenyl group, m-chlorophenyl group, p-chlorophenyl group, o-methylphenyl group, m-methylphenyl group, and p-methylphenyl group. Suitable values for an optionally substituted $C_{7-10}$ aralkyl group include, for example, a benzyl group, o-methoxybenzyl group, m-methoxybenzyl group, p-methoxybenzyl group, o-nitrobenzyl, m-nitrobenzyl, p-nitrobenzyl, o-chlorobenzyl group, m-chlorobenzyl group, p-chlorobenzyl group, o-methylbenzyl group, m-methylbenzyl group, and p-methylbenzyl group.

In particular one or both of $R^8$ and $R^9$ are methyl group or ethyl group, and preferably both of $R^8$ and $R^9$ are methyl group or ethyl group.

In the compound of formula (13), values of substituents $R^7$, $R^8$ originate from respective values in the styrene oxide derivative of formula (14) or a halohydrin derivative represented by the formula (15) and carboxylate ester derivative represented by general formula (16). In other words, $R^7$ denotes an aryl group substituted by 2 or more halogen atoms, and $R^8$ denotes optionally substituted $C_{1-10}$ cyclic or acyclic alkyl group, optionally substituted $C_{6-10}$ aryl group, or optionally substituted $C_{7-10}$ aralkyl group, and $R^9$ denotes optionally substituted $C_{1-10}$ cyclic or acyclic alkyl group, optionally substituted $C_{6-10}$ aryl group, or optionally substituted $C_{7-10}$ aralkyl group. Suitable values for an aryl group substituted by 2 or more halogen atoms, include, for example, a 2,3-difluorophenyl group, 3,4-difluorophenyl group, 2,4-difluorophenyl group, 2,3,4-trifluorophenyl group, 3,4,5-trifluorophenyl group, 2,3,4,5-tetrafluorophenyl group, 2,3,4,5,6-pentafluorophenyl group, 2,3-dichlorophenyl group, 3,4-dichlorophenyl group, 2,4-dichlorophenyl group, 2,3,4-trichlorophenyl group, 3,4,5-trichlorophenyl group, 2,3,4,5-tetrachlorophenyl group, 2,3,4,5,6-pentachlorophenyl group, 2,3-dibromophenyl group, 3,4-dibromophenyl group, 2,4-dibromophenyl group, 2,3,4-tribromophenyl group, 3,4,5-tribromophenyl group, 2,3,4,5-tetrabromophenyl group, and 2,3,4,5,6-pentabromo phenyl group. Suitable values for a $C_{1-10}$ cyclic or acyclic alkyl group, include, for example, a methyl group, ethyl group, n-propyl group, i-propyl group, cyclopropyl group, n-butyl group, s-butyl group, i-butyl group, t-butyl group, cyclobutyl group, n-pentyl group, neopentyl group, cyclopentyl group, n-hexyl group, cyclohexyl group, n-heptyl group, cyclohexylmethyl group, n-octyl group, and n-decyl group. Suitable values for an optionally substituted $C_{6-10}$ aryl group include, for example, a phenyl group, o-methoxyphenyl group, m-methoxyphenyl group, p-dimethoxy phenyl group, o-nitrophenyl group, m-nitrophenyl group, p-nitrophenyl group, o-chlorophenyl group, m-chlorophenyl group, p-chlorophenyl group, o-methylphenyl group, m-methylphenyl group, and p-methylphenyl group. Suitable values for an optionally substituted $C_{7-10}$ aralkyl group include, for example, a benzyl group, o-methoxybenzyl group, m-methoxybenzyl group, p-methoxybenzyl group, o-nitrobenzyl, m-nitrobenzyl, p-nitrobenzyl, o-chlorobenzyl group, m-chlorobenzyl group, p-chlorobenzyl group, o-methylbenzyl group, m-methylbenzyl group, and p-methylbenzyl group. It is generally preferred that $R^7$ is a 3,4-difluorophenyl group and $R^8$ is an ethyl group.

Moreover, * denotes an asymmetric carbon centre. In other words, an ester derivative represented by the formula (13) contains asymmetric carbon centres. The invention includes any optically active substance or racemic mixture of the compound of formula (13). Preferably it is an optically active substance, and most preferably it is a compound whose absolute configuration of asymmetric carbon centre is (1R, 2R).

The optically active halohydrin derivative represented by the formula (15) which is a starting material of this invention can be readily obtained, for example, by enantioselectively reacting a α-halomethyl arylketone derivative obtained by reacting a benzene derivative with α-halo acetic acid chloride in the presence of aluminum chloride. The optically active styrene oxide derivative of formula (14) can be readily obtained by epoxidation of an optically active α-halohydrin derivative of formula (15).

A compound of formula (14) or of formula (15) is reacted with a compound of formula (16) in the presence of base and thereby converted to compound of formula (13). Examples of suitable bases include, for example, an organolithium compound such as methyllithium, n-butyllithium, t-butyllithium, phenyl lithium or the like, a Grignard reagent such as n-butylmagnesiumchloride, methyl magnesium bromide or the like; an alkaline earth metal amide or alkali metal amide such as lithium amide, sodium amide, lithium diisopropyl amide, magnesium diisopropyl amide, lithium hexamethyl disilazide, sodium hexamethyl disilazide, potassium hexamethyl disilazide or the like; an alkali metal alkoxide such as sodium methoxide, sodium ethoxide, sodium-t-butoxide, lithium methoxide, lithium ethoxide, lithium-t-butoxide, potassium-t-butoxide or the like; an alkaline earth metal hydride or alkali metal hydride such as lithium hydride, sodium hydride, potassium hydride, calcium hydride or the like.

A base of an alkali metal-t-butoxide, alkali metal hydride or the like is generally preferred.

The quantity of base used differs depending on species of base used, species of solvent and reaction conditions. A particular quantity is a 1-5 fold molar ratio, preferably 1-3 fold molar ratio with respect to compound of formula (14) or (15).

The quantity of compound of formula (16) used differs depending on species of solvent and reaction conditions. A particular quantity is a 1-5 fold molar ratio, preferably 1-3 fold molar ratio with respect to compound of formula (14) or (15).

In general, a solvent is usually used in the reaction. Examples include, for example, dichloromethane, chloroform, dichloroethane, benzene, toluene, diethyl ether, ethylene glycol dimethylether, methyl-t-butyl ether, diisopropyl ether, tetrahydrofuran, 1,4-dioxane, N,N-dimethylformamide, N-methylpyrrolidone, 1,3-dimethyl imidazolidinone, dimethylsulfoxide, acetone, acetonitrile, ethyl acetate, isopropyl acetate ester, acetic acid-t-butyl, t-butanol, and the like. The solvent may be used alone or as an admixture thereof, and in this case, the mixed proportions thereof are not restricted.

A solvent of toluene, ethylene glycol dimethylether, tetrahydrofuran or 1,4-dioxane is generally preferred.

Suitable values of the reaction temperature include values selected from the range of −30° C. to boiling point of solvent used, and a temperature in the range of 20° C.-90° C. Generally, the reaction time required is usually 30 minutes to 24 hours.

On completion of the reaction, solvent may be removed by distillation. The reaction mixture may then be added to water or water is added to it, and thereafter, it may be neutralized by addition of an appropriate quantity of acid. The compound of formula (13) may be obtained by using procedures such as extraction with an organic solvent such as toluene, ethyl acetate, isopropyl acetate, diethyl ether, dichloromethane, chloroform or the like, washing with water and concentration. The compound obtained may be purified further by column chromatography or distillation.

Examples of the acid used for neutralization after completion of the reaction include, but are not limited to, organic carboxylic acid such as formic acid, acetic acid, propionic acid, trifluoroacetic acid, chloroacetic acid, dichloroacetic acid, trichloroacetic acid, oxalic acid, benzoic acid, phthalic acid, fumaric acid, mandelic acid or the like; an optically active organic carboxylic acid such as tartaric acid, lactic acid, ascorbic acid, amino acid or the like; an organic sulfonic acid such as methanesulfonic acid, trifluoromethanesulfonic acid, benzenesulfonic acid, p-toluenesulfonic acid, camphor sulfonic acid or the like; an inorganic acid such as hydrochloric acid, sulphuric acid, nitric acid, phosphoric acid, carbonic acid or the like. Hydrochloric acid or sulfuric acid are generally preferred.

Next, there will be described 2) deesterification process.

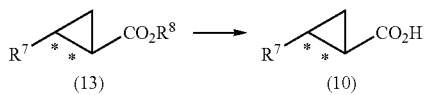

Step 2. Deesterification Process

The values of $R^7$, $R^8$ and * in the compound of formula (13), including the suitable and preferred values, are the same as those mentioned above in 1) cyclopropanation process. In the compound of formula (10), the values of substituent $R^7$ including the suitable and preferred values, originate from the ester derivative of formula (13). In other words, $R^7$ denotes an aryl group substituted by 2 or more halogen atoms. Suitable values of an aryl group substituted by 2 or more halogen atoms include, for example, a 2,3-difluorophenyl group, 3,4-difluorophenyl group, 2,4-difluorophenyl group, 2,3,4-trifluorophenyl group, 3,4,5-trifluorophenyl group, 2,3,4,5-tetrafluorophenyl group, 2,3,4,5,6-pentafluorophenyl group, 2,3-dichlorophenyl group, 3,4-dichlorophenyl group, 2,4-dichlorophenyl group, 2,3,4-trichlorophenyl group, 3,4,5-trichlorophenyl group, 2,3,4,5-tetrachlorophenyl group, 2,3,4,5,6-pentachlorophenyl group, 2,3-dibromophenyl group, 3,4-dibromophenyl group, 2,4-dibromophenyl group, 2,3,4-tribromophenyl group, 3,4,5-tribromophenyl group, 2,3,4,5-tetrabromophenyl group or 2,3,4,5,6-pentabromophenyl group. A 3,4-difluorophenyl group is generally preferred.

Moreover, * denotes an asymmetric carbon centre. In other words the carboxylic acid derivative of formulae (10) contains asymmetric carbon centres. The invention includes any optically active substance or racemic mixture of the compound of formula (10). Preferably it is an optically active substance, and most preferably it is a compound whose absolute configuration of asymmetric carbon centre is (1R, 2R).

In this step, the compound of formula (13) is converted to the compound of formula (10) by deesterifying, and reaction conditions of deesterification of Compound (13) are not restricted. The reaction may be carried out using general deesterification conditions. Examples of conditions for deesterification include a process of oxidative elimination of p-methoxybenzyl ester using DDQ (2,3-dichloro-5,6-dicyanobenzoquinone) and CAN (cerium nitrate), a process to eliminate benzyl ester, t-butyl ester using iodotrimethylsilane, a process of reductive elimination of benzyl ester using palladium catalyst under a hydrogen atmosphere, a process to eliminate t-butyl ester using TFA (trifluoroacetic acid), a process to eliminate ester group by acid or alkali hydrolysis, or the like. From the point of inexpensiveness and the point that the process can be applied for most kinds of ester group, the process to eliminate ester group by acid or alkali hydrolysis is preferred, and the process to eliminate ester group by alkali hydrolysis is more preferred.

Suitable alkalis include an alkali metal hydroxide such as lithium hydroxide, sodium hydroxide, potassium hydroxide, cesium hydroxide or the like; an alkaline earth metal hydroxide such as magnesium hydroxide, calcium hydroxide, barium hydroxide or the like; an alkali metal carbonate such as lithium carbonate, sodium carbonate, potassium carbonate, cesium carbonate or the like. An inorganic acid such as hydrochloric acid, sulphuric acid, nitric acid, phosphoric acid, perchloric acid or the like are generally preferred.

Suitable reaction solvents for deesterification include, for example, water, tetrahydrofuran, 1,4-dioxane, diethyl ether, methyl-t-butyl ether, toluene, benzene, N,N-dimethylformamide, dimethylsulfoxide, dichloromethane, chloroform, acetone, acetonitrile, butanol, propanol, ethanol, methanol, water and the like. The solvent may be used alone or as a mixture thereof, and in this case, the mixed proportions are not limited in particular.

In general, a solvent of toluene, tetrahydrofuran, ethanol or methanol is preferred.

Suitable reaction temperatures, include those selected from the range of −30° C. to boiling point of solvent used, and preferably it is 0° C.-80° C. The reaction time is required usually to be 30 minutes to 27 hours.

On completion of the reaction, the solvent may be removed by distillation, and thereafter the mixture added to water or water is added to it as required. The mixture is neutralized by addition of acid. The compound of formula (10) may be obtained by procedures such as extraction with an organic solvent such as toluene, ethyl acetate, isopropyl acetate, diethyl ether, dichloromethane, chloroform or the like; washing with water, concentration and the like. The obtained compound may be further purified by column chromatography or crystallisation, or it may be used in the following step without treatment.

Suitable acids used for neutralization after completion of the reaction include, for example, an organic carboxylic acid such as formic acid, acetic acid, propionic acid, trifluoroacetic acid, chloroacetic acid, dichloroacetic acid, trichloroacetic acid, oxalic acid, benzoic acid, phthalic acid, fumaric acid, mandelic acid or the like; an optically active organic carboxylic acid such as tartaric acid, lactic acid, ascorbic acid, amino acid or the like; an organic sulfonic acid such as methanesulfonic acid, trifluoromethanesulfonic acid, benzenesulfonic acid, p-toluenesulfonic acid, camphor sulfonic acid or the like; an inorganic acid such as hydrochloric acid, sulphuric acid, nitric acid, phosphoric acid, carbonic acid or the like. Hydrochloric acid and sulfuric acid are generally preferred.

Next, a description will be given of 3) amidation process.

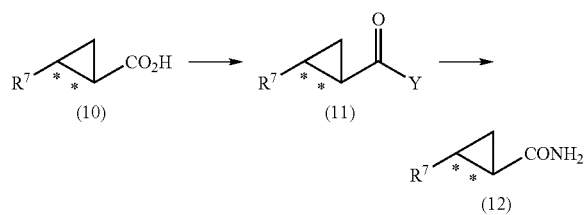

Step 3. Amidation Process

In the compound of formula (10), the values of substituent $R^7$ and * (including the suitable and preferred values) are the same as those mentioned above in 2) deesterification process.

In the compound of formula (11), values of substituent $R^7$ originate from the ester derivative of formula (10). In other words, $R^7$ may represent an aryl group substituted by 2 or more halogen atoms. Suitable values for an aryl group substituted by 2 or more halogen atoms include a 2,3-difluorophenyl group, 3,4-difluorophenyl group, 2,4-difluorophenyl group, 2,3,4-trifluorophenyl group, 3,4,5-trifluorophenyl group, 2,3,4,5-tetrafluorophenyl group, 2,3,4,5,6-pentafluorophenyl group, 2,3-dichlorophenyl group, 3,4-dichlorophenyl group, 2,4-dichlorophenyl group, 2,3,4-trichlorophenyl group, 3,4,5-trichlorophenyl group, 2,3,4,5-tetrachlorophenyl group, 2,3,4,5,6-pentachlorophenyl group, 2,3-dibromophenyl group, 3,4-dibromophenyl group, 2,4-dibromophenyl group, 2,3,4-tribromophenyl group, 3,4,5-tribromophenyl group, 2,3,4,5-tetrabromophenyl group, 2,3,4,5,6-pentabromo phenyl group or the like. A 3,4-difluorophenyl group is generally preferred. Moreover, Y denotes an activated carbonyl group activated group, and it is derived from the carboxylic acid activator described later.

Moreover, * denotes an asymmetric carbon centre. In other words the carboxylic acid derivative of formula (11) contains asymmetric carbon centres. The invention includes any optically active substance or racemic mixture of the compound of formula (11). Preferably it is an optically active substance, and most preferably it is a compound whose absolute configuration of asymmetric carbon centre is (1R, 2R).

In the compound of formula (12), values of substituent $R^7$ originate from the ester derivative of formula (10). In other words, $R^7$ may denote an aryl group substituted by 2 or more halogen atoms. Suitable values for an aryl group substituted by 2 or more halogen atoms include a 2,3-difluorophenyl group, 3,4-difluorophenyl group, 2,4-difluorophenyl group, 2,3,4-trifluorophenyl group, 3,4,5-trifluorophenyl group, 2,3,4,5-tetrafluorophenyl group, 2,3,4,5,6-pentafluorophenyl group, 2,3-dichlorophenyl group, 3,4-dichlorophenyl group, 2,4-dichlorophenyl group, 2,3,4-trichlorophenyl group, 3,4,5-trichlorophenyl group, 2,3,4,5-tetrachlorophenyl group, 2,3,4,5,6-pentachlorophenyl group, 2,3-dibromophenyl group, 3,4-dibromophenyl group, 2,4-dibromophenyl group, 2,3,4-tribromophenyl group, 3,4,5-tribromophenyl group, 2,3,4,5-tetrabromophenyl group, 2,3,4,5,6-pentabromo phenyl group or the like. A 3,4-difluorophenyl group is generally preferred.

Moreover, * denotes an asymmetric carbon centre. In other words, the carboxylic acid derivative of formula (12) contains asymmetric carbon centres. The invention includes any optically active substance or racemic mixture of the compound of formula (12). Preferably, it is an optically active substance, and most preferably it is a compound whose absolute configuration of asymmetric carbon centre is (1R, 2R).

The compound of formula (10) may be formed into the compound of formula (11) by reacting with a carboxylic acid activator to activate the carbonyl moiety. The activated compound is converted to the compound of formula (12) by reacting with ammonia. Suitable carboxylic acid activators include, for example, a dehydrocondensation agent such as dicyclohexylcarbodiimide (DCC) and carbonyldiimidazole; chlorocarbonic acid esters such as methyl chlorocarbonate ester, ethyl chlorocarbonate ester, propyl chlorocarbonate ester, isopropyl chlorocarbonate ester, chlorocarbonate butyl ester, t-butyl chlorocarbonate, benzyl chlorocarbonate or the like; an acid anhydride such as acetic anhydride, anhydrous trifluoroacetic acid, anhydrous methanesulfonic acid, anhydrous trifluoromethanesulfonic acid or the like; an carboxylic acid ester species such as carbonic acid di-t-butyl, dimethyl carbonate, diethyl carbonate or the like, acid chloride such as methanesulfonyl chloride, p-toluenesulphonyl chloride, phosphorus pentachloride, phosphorus trichloride, phosphorus oxychloride, acetyl chloride, propionyl chloride, pivaloyl chloride, benzoyl chloride, thionyl chloride, chlorosulfuric acid, oxalyl chloride; phosgene or the like, and a metal chloride such as titanium chloride, aluminum chloride, ferric chloride or the like may be proposed.

Particular carboxylic acid activators are chlorocarbonate ester, acid anhydride, carboxylic acid ester, acid chloride except phosgene. In general thionyl chloride is preferred particularly as it offers advantages from the point of handling and post-treatment after reaction.

The quantity used of carboxylic acid activator differs depending on species of base used and species of solvent and of reaction conditions. In particular a 1-3 fold molar ratio may be used, and preferably a 1-1.5 fold molar ratio with respect to compound represented by the aforesaid formula (10).

When reacting the compound of formula (10) with the carboxylic acid activator, a base may be used in accordance with requirements. Suitable bases include, for example, an organolithium compound such as methyllithium, n-butyllithium, t-butyllithium, phenyl lithium or the like, a Grignard reagent such as n-butyl magnesium chloride, methyl magnesium bromide or the like, alkaline earth metal amide or alkali metal amide such as lithium amide, sodium amide, lithium diisopropyl amide, magnesium diisopropyl amide, lithium hexamethyl disilazide, sodium hexamethyl disilazide, potassium hexamethyl disilazide or the like, alkali metal alkoxide such as sodium methoxide, sodium ethoxide, sodium-t-butoxide, lithium methoxide, lithium ethoxide, lithium-t-butoxide, potassium-t-butoxide or the like, alkaline earth metal hydride or alkali metal hydride such as lithium hydride, sodium hydride, potassium hydride, calcium hydride or the like, alkaline earth metal hydroxide or alkali metal hydroxide such as lithium hydroxide, sodium hydroxide, potassium hydroxide, cesium hydroxide, magnesium hydroxide, calcium hydroxide or the like, alkali metal carbonate such as lithium carbonate, sodium carbonate, potassium carbonate or the like, alkali metal bicarbonate such as lithium bicarbonate, sodium bicarbonate, potassium bicarbonate or the like, organic tertiary amine such as triethylamine, diisopropyl ethylamine, DBU (1,8-diazabicyclo[5,4,0]undecene) or the like, basic organic solvent such as N,N-dimethylformamide or the like.

In particular, the base may be an alkali metal alkoxide, alkaline earth metal hydride or alkali metal hydride, alkaline earth metal hydroxide or alkali metal hydroxide, alkaline earth carbonate or alkali metal carbonate, alkali metal bicarbonate, or organic tertiary amine. In general an alkaline earth metal hydroxide or alkali metal hydroxide, alkaline earth carbonate or alkali metal carbonate, alkali metal bicarbonate, organic tertiary amine or the like is preferred.

The quantity used of base differs depending on the species of base used and species of solvent and reaction conditions. In particular a 1-3 fold molar ratio may be used, and preferably a 1-1.5 fold molar ratio with respect to compound represented by the aforesaid formula (10).

Suitable forms of the ammonia used include, for example, liquid ammonia, ammonia gas, ammonia solution in organic solvent and ammonia water. Particular examples are ammonia gas, ammonia in an organic solvent, ammonia water, and ammonia water is generally preferred.

When the form of ammonia is ammonia water the concentration of ammonia water used is not limited. In particular 5-30 wt % may be used, and 20-28 wt % is generally preferred.

The quantity of ammonia used differs depending on the form of used ammonia, species of solvent and reaction conditions. In particular, a 1-6 fold molar ratio may be used, and, preferably, a 3-5 fold molar ratio with respect to compound represented by the aforesaid formula (10).

Generally a solvent is usually used in the reaction. Suitable solvents include for example dichloromethane, chloroform, dichloroethane, benzene, toluene, diethyl ether, methyl-t-butyl ether, diisopropyl ether, tetrahydrofuran, 1,4-dioxane, N,N-dimethylformamide, N-methylpyrrolidone, 1,3-dimethyl imidazolidinone, dimethylsulfoxide, acetone, acetonitrile, ethyl acetate, isopropyl acetate ester and acetic acid-t-butyl and the like.

The solvent may be used alone or by mixing, and in this case, the mixing proportion is not limited. Generally a solvent of toluene, ethyl acetate and isopropyl acetate are preferred.

Suitable reaction temperatures, include those selected from the range of −30° C. to boiling point of solvent used and preferably it is selected from the range of 0° C.-60° C. The reaction time required is usually 10 minutes to 24 hours.

On completion of the reaction, the solvent is removed by distillation in accordance with requirements, and thereafter the reaction mixture is added to water or water is added to it. The compound of formula (12) is obtained using procedures such as extraction with an organic solvent such as toluene, ethyl acetate, isopropyl acetate ester, diethyl ether, dichloromethane, chloroform or the like, washing with water, and concentration. The obtained compound may be further purified by column chromatography or crystallisation, or it may be used in the following step without treatment.

The compound of formula (17)

(17)

produced by the aforesaid process is a novel compound, and is therefore provided as a further feature of the present invention. In formula (17), $R^{10}$ denotes an aryl group substituted by 2 or more halogen atoms. Suitable values for the aryl group substituted by 2 or more halogen atoms include a 2,3-difluorophenyl group, 3,4-difluorophenyl group, 2,4-difluorophenyl group, 2,3,4-trifluorophenyl group, 3,4,5-trifluorophenyl group, 2,3,4,5-tetrafluorophenyl group, 2,3,4,5,6-pentafluorophenyl group, 2,3-dichlorophenyl group, 3,4-dichlorophenyl group, 2,4-dichlorophenyl group, 2,3,4-trichlorophenyl group, 3,4,5-trichlorophenyl group, 2,3,4,5-tetrachlorophenyl group, 2,3,4,5,6-pentachlorophenyl group, 2,3-dibromophenyl group, 3,4-dibromophenyl group, 2,4-dibromophenyl group, 2,3,4-tribromophenyl group, 3,4,5-tribromophenyl group, 2,3,4,5-tetrabromophenyl group, 2,3,4,5,6-pentabromo phenyl group or the like. A 3,4-difluorophenyl group is generally preferred.

Moreover, * denotes an asymmetric carbon centre. In other words, the carboxamide derivative of formulae (17) contains asymmetric carbon centres. The invention includes any optically active substance or racemic mixture of the compound of formula (17). Preferably it is optically active substance, and most preferably it is a compound whose absolute configuration of asymmetric carbon centre is (1R, 2R).

Next, a description will be given of 4) Hofmann rearrangement process.

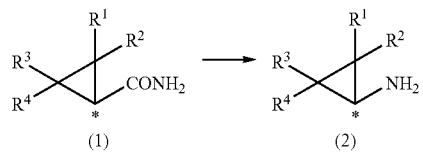

Step 4. Hofmann Rearrangement Step

In the compound of formula (1), $R^1$, $R^2$, $R^3$ and $R^4$ each independently denote hydrogen atom, optionally substituted $C_{1-10}$ cyclic or acyclic alkyl group, optionally substituted $C_{6-10}$ aryl group or optionally substituted $C_{7-10}$ aralkyl group, and they may be the same or different to each other. Suitable values of an optionally substituted cyclic or acyclic alkyl group of carbon number 1-10 include a methyl group, ethyl group, n-propyl group, i-propyl group, cyclopropyl group, n-butyl group, s-butyl group, i-butyl group, t-butyl group, cyclobutyl group, n-pentyl group, neopentyl group, cyclopentyl group, n-hexyl group, cyclohexyl group, n-heptyl group, cyclohexylmethyl group, n-octyl group, n-decyl group and the like. Suitable values of an optionally substituted $C_{6-10}$ aryl group include a phenyl group, o-methoxyphenyl group, m-methoxyphenyl group, p-dimethoxy phenyl group, o-nitrophenyl group, m-nitrophenyl group, p-nitrophenyl group, o-fluorophenyl group, m-fluorophenyl group, p-fluorophenyl group, o-chlorophenyl group, m-chlorophenyl group, p-chlorophenyl group, 2,3-difluorophenyl group, 3,4-difluorophenyl group, 2,4-difluorophenyl group, 2,3,4-trifluorophenyl group, 3,4,5-trifluorophenyl group, 2,3,4,5-tetrafluorophenyl group, 2,3,4,5,6-pentafluorophenyl group, 2,3-dichlorophenyl group, 3,4-dichlorophenyl group, 2,4-dichlorophenyl group, 2,3,4-trichlorophenyl group, 3,4,5-trichlorophenyl group, 2,3,4,5-tetrachlorophenyl group, 2,3,4,5,6-pentachlorophenyl group, 2,3-dibromophenyl group, 3,4-dibromophenyl group, 2,4-dibromophenyl group, 2,3,4-tribromophenyl group, 3,4,5-tribromophenyl group, 2,3,4,5-tetrabromophenyl group, 2,3,4,5,6-pentabromo phenyl group, o-methylphenyl group, m-methylphenyl group, p-methylphenyl group and the like. Suitable values of an optionally substituted $C_{7-10}$ aralkyl group include a benzyl group, o-methoxybenzyl group, m-methoxybenzyl group, p-methoxybenzyl group, o-nitrobenzyl group, m-nitrobenzyl group, p-nitrobenzyl group, o-chlorobenzyl group, m-chlorobenzyl group, p-chlorobenzyl group, o-methylbenzyl group, m-methylbenzyl group, p-methylbenzyl group and the like. Preferably any of $R^1$, $R^2$, $R^3$ and $R^4$ is a 3,4-difluorophenyl group, and more preferably the substituent except 3,4-difluorophenyl group is a hydrogen atom.

Moreover, * denotes an asymmetric carbon centre. In other words, the compound of formula (1) has asymmetric carbon centre. The invention includes any optically active substance or racemic mixture of the compound of formula (1). Preferably it is optically active substance, and most preferably it is a compound whose absolute configuration of asymmetric carbon centre is (1R, 2R).

In the compound of formula (2), values (including suitable and preferred) for $R^1$, $R^2$, $R^3$ and $R^4$ originate from the compound of formula (1). In other words, $R^1$, $R^2$, $R^3$ and $R^4$ each independently denote a hydrogen atom, an optionally substituted $C_{1-10}$ cyclic or an acyclic alkyl group, optionally substituted $C_{6-10}$ aryl group, or optionally substituted $C_{7-10}$ aralkyl group, and they may be the same or different to each other. Suitable values for an optionally substituted $C_{1-10}$ cyclic or acyclic alkyl group include a methyl group, ethyl group, n-propyl group, i-propyl group, cyclopropyl group, n-butyl group, s-butyl group, i-butyl group, t-butyl group, cyclobutyl group, n-pentyl group, neopentyl group, cyclopentyl group, n-hexyl group, cyclohexyl group, n-heptyl group, cyclohexylmethyl group, n-octyl group, n-decyl group and the like. Suitable values for an optionally substituted $C_{6-10}$ aryl group include a phenyl group, o-methoxyphenyl group, m-methoxyphenyl group, p-dimethoxy phenyl group, o-nitrophenyl group, m-nitrophenyl group, p-nitrophenyl group, o-fluorophenyl group, m-fluorophenyl group, p-fluorophenyl group, o-chlorophenyl group, m-chlorophenyl group, p-chlorophenyl group, 2,3-difluorophenyl group, 3,4-difluorophenyl group, 2,4-difluorophenyl group, 2,3,4-trifluorophenyl group, 3,4,5-trifluorophenyl group, 2,3,4,5-tetrafluorophenyl group, 2,3,4,5,6-pentafluorophenyl group, 2,3-dichlorophenyl group. 3,4-dichlorophenyl group, 2,4-dichlorophenyl group, 2,3,4-trichlorophenyl group, 3,4,5-trichlorophenyl group, 2,3,4,5-tetrachlorophenyl group, 2,3,4,5,6-pentachlorophenyl group, 2,3-dibromophenyl group, 3,4-dibromophenyl group, 2,4-dibromophenyl group, 2,3,4-tribromophenyl group, 3,4,5-tribromophenyl group, 2,3,4,5-tetrabromophenyl group, 2,3,4,5,6-penta bromo phenyl group, o-methylphenyl group, m-methylphenyl group, p-methylphenyl group and the like. Suitable values for an optionally substituted $C_{7-10}$ aralkyl group include a benzyl group, o-methoxybenzyl group, m-methoxybenzyl group, p-methoxybenzyl group, o-nitrobenzyl group, m-nitrobenzyl group, p-nitrobenzyl group, o-chlorobenzyl group, m-chlorobenzyl group, p-chlorobenzyl group, o-methylbenzyl group, m-methylbenzyl group, p-methylbenzyl group and the like. Wherein preferably any of $R^1$, $R^2$, $R^3$ and $R^4$ is a 3,4-difluorophenyl group, and more preferably, the substituent other than 3,4-difluorophenyl group is hydrogen atom.

Moreover, * denotes an asymmetric carbon centre. In other words, the compound represented by the formula (2) has asymmetric carbon centre. The invention includes any optically active substance or racemic mixture of the compound of formula (2). Preferably it is optically active substance, and most preferably it is a compound whose absolute configuration of asymmetric carbon centre is (1R, 2S).

When oxidant is caused to act, there proceeds a so-called Hofmann rearrangement, and the compound of formula (1) is converted to the compound of formula (2) while maintaining the stereochemistry of the asymmetric carbon centre represented by *. For example, suitable oxidants include a high valency iodine reagent exemplified by bis (trifluoroacetoxy) phenyl iodide, halide agent such as chlorine, bromine, iodine, N-chlorosuccinimide, N-bromosuccinimide, N-iodosuccinimide, sulphuryl chloride, sulphuryl bromide or the like, hypochlorite species such as lithium hypochlorite, sodium hypochlorite, potassium hypochlorite, magnesium hypochlorite, calcium hypochlorite or the like may be proposed, and chlorine, N-chloro succinimide, hypochlorite species or the like. In general sodium hypochlorite is preferred.

The quantity of oxidant used differs depending on species of oxidant used, species of reaction solvent and reaction conditions. In particular a 1-5 fold molar ratio may be used and preferably a 2-4 fold molar ratio with respect to the compound of formula (1). Moreover, as regards the quantity used of the aforesaid oxidant, when a hypochlorite species is used as the oxidant, the quantity used is determined by effective chlorine conversion.

In the reaction of compound of formula (1) and oxidant, a base may be co-present in accordance with requirements. Base may be added after mixing the compound of formulae (1) and oxidant. Suitable bases include, for example, an organolithium compound such as methyllithium, n-butyllithium, t-butyllithium, phenyl lithium or the like, Grignard reagent such as n-butylmagnesium chloride, methyl magnesium bromide or the like, alkaline earth metal amide or alkali metal amide such as lithium amide, sodium amide, lithium diisopropyl amide, magnesium diisopropyl amide, lithium hexamethyl disilazide, sodium hexamethyl disilazide, potassium hexamethyl disilazide or the like, alkali metal alkoxide such as sodium methoxide, sodium ethoxide, sodium-t-butoxide, lithium methoxide, lithium ethoxide, lithium-t-butoxide, potassium-t-butoxide or the like, alkaline earth metal hydride or alkali metal hydride such as lithium hydride, sodium hydride, potassium hydride, calcium hydride or the like, alkaline earth metal hydroxide or alkali metal hydroxide such as lithium hydroxide, sodium hydroxide, potassium hydroxide, cesium hydroxide, magnesium hydroxide, calcium hydroxide or the like, alkali metal carbonate such as lithium carbonate, sodium carbonate, potassium carbonate or the like, alkali metal bicarbonate such as lithium bicarbonate, sodium bicarbonate, potassium bicarbonate or the like, organic tertiary amine such as triethylamine, diisopropyl ethylamine, DBU (1,8-diazabicyclo[5,4,0]undecene) or the like.

In general an alkali metal hydroxide such as sodium hydroxide is the preferred.

The quantity of base used differs depending on species of base used, species of solvent and reaction conditions. In particular the reaction may be caused to proceed in high yield by using a 5-30 fold molar ratio, preferably 5-20 fold molar ratio with respect to compound represented by general formula (2).

In particular the concentration of the base in the reaction may be in the range of 5-30 wt %, more particularly in the range of 15-25 wt %.

In general a solvent is usually used in the reaction. Suitable solvents include, for example, water, dichloromethane, chloroform, dichloroethane, benzene, toluene, diethyl ether, methyl-t-butyl ether, tetrahydrofuran, 1,4,-dioxane, N,N-dimethylformamide, N-methylpyrrolidone, 1,3-dimethyl imidazolidinone, dimethylsulfoxide, acetone, acetonitrile, ethyl acetate, acetic acid-t-butyl, t-butanol and the like.

The solvent may be used alone or as a mixture. In the case of a mixture the proportion is not limited. In general, water is preferred.

Suitable reaction temperatures include those selected from the range of −30° C. to boiling point of solvent used and preferably it is selected from the range of 20° C.-60° C. The reaction time required is usually 30 minutes to 24 hours.

On completion of the reaction the solvent may be removed by distillation. The reaction mixture may be added to water or water to it, and then the mixture is acidified by addition of acid. The Compound (2) is transferred to the aqueous layer, and after having been caused to undergo liquid separation and washing with organic solvent such as toluene, ethyl acetate, isopropyl acetate, diethyl ether, dichloromethane, chloroform or the like, the aqueous layer is made basic using a base. The Compound of formula (2) is obtained using procedures such as extraction with an organic solvent such as toluene, ethyl acetate, isopropyl acetate, diethyl ether, dichloromethane, chloroform or the like, washing with water and concentration. Usually, on completion of the reaction, solvent is removed by distillation, and the compound of formula (2) may be obtained via procedures such as extraction with organic solvent such as toluene, ethyl acetate, isopropyl acetate, diethyl ether, dichloromethane, chloroform or the like, washing with water and concentration without the step of transfering to the aqueous layer. The compound (2) may be obtained in the form of a salt of an acid. The compound may be further purified by column chromatography, distillation or crystallisation, or it may be separated and purified in the form of a salt of an acid.

Suitable acids used after completion of the reaction include, for example, an organic carboxylic acid such as formic acid, acetic acid, propionic acid, trifluoroacetic acid, chloroacetic acid, dichloroacetic acid, trichloroacetic acid, oxalic acid, benzoic acid, phthalic acid, fumaric acid, mandelic acid or the like, optically active organic carboxylic acid such as tartaric acid, lactic acid, ascorbic acid, amino acid or the like, organic sulfonic acid such as methanesulfonic acid, trifluoromethanesulfonic acid, benzenesulfonic acid, p-toluenesulfonic acid, camphor sulfonic acid or the like, inorganic acid such as hydrochloric acid, sulphuric acid, nitric acid, phosphoric acid, carbonic acid. Hydrochloric acid or sulfuric acid are generally preferred.

Suitable bases used after completion of the reaction include, for example, an organolithium compound such as methyllithium, n-butyllithium, t-butyllithium, phenyl lithium or the like, Grignard reagent such as n-butylmagnesium chloride, methyl magnesium bromide or the like, alkaline earth metal amide or alkali metal amide such as lithium amide, sodium amide, lithium diisopropyl amide, magnesium diisopropyl amide, lithium hexamethyl disilazide, sodium hexamethyl disilazide, potassium hexamethyl disilazide or the like, alkali metal alkoxide such as sodium methoxide, sodium ethoxide, sodium-t-butoxide, lithium methoxide, lithium ethoxide, lithium-t-butoxide, potassium-t-butoxide or the like, alkaline earth metal hydride or alkali metal hydride such as lithium hydride, sodium hydride, potassium hydride, calcium hydride or the like, alkaline earth metal hydroxide or alkali metal hydroxide such as lithium hydroxide, sodium hydroxide, potassium hydroxide, cesium hydroxide, magnesium hydroxide, calcium hydroxide or the like, alkali carbonate metal salt such as lithium carbonate, sodium carbonate, potassium carbonate or the like, alkali metal bicarbonate such as lithium bicarbonate, sodium bicarbonate, potassium bicarbonate or the like, organic tertiary amine or the like such as triethylamine, diisopropyl ethylamine, DBU (1,8-diazabicyclo[5,4,0]undecene).

In general an alkali metal hydroxide, alkaline earth metal hydroxide, alkali carbonate metal salt, alkaline earth metal carbonate, alkali metal bicarbonate alkaline earth metal carbonate, organic tertiary amine are preferred.

Any of the embodiments described herein can be combined with any of the other embodiments described herein.

In order that the invention disclosed herein may be more efficiently understood, examples are provided below. It should be understood that these examples are for illustrative purposes only and are not to be construed as limiting the invention in any manner.

EXAMPLES

Example 1

Preparation of (2S)-2-(3,4-difluorophenyl)oxirane

A mixture of (1S)-2-chloro-1-(3,4-difluorophenyl)-1-ethanol (net 11.47 g, 59.5 mmol), toluene (25.23 g), sodium hydroxide (2.53 g, 1.06 molar equivalents) and water (24.25 g) was stirred and heated at 40° C. for 1 hour. The organic layer was separated, washed with water, and concentrated under reduced pressure. (2S)-2-(3,4-difluorophenyl)oxirane was obtained as resultant concentrate (net 8.94 g, yield: 96%).

$^1$H-NMR in (400 MHz, CDCl3)

δ 2.71-2.73 (1H, dd, J=2.44 Hz, 5.37 Hz), 3.13-3.15 (1H, m), 3.82-3.83 (1H, m), 7.01-7.27 (4H, m).

Example 2

Preparation of ethyl (1R,2R)-2-(3,4-difluorophenyl)-1-cyclopropanecarboxylate

Sodium t-butoxide (32.22 g, 1.25 molar equivalents) and toluene (243.0 g) were charged into a reaction vessel. Triethyl phosphonoacetate (78.06 g, 1.04 molar equivalents to sodium t-butoxide) was added to the mixture with stirring. A toluene solution of (2S)-2-(3,4-difluorophenyl)oxirane (32.8 wt % solution, net 41.83 g, 267.9 mmol) was added drop-wise to the mixture keeping the internal temperature between 60 to 80° C. After completion of addition, stirring was continued for 11 hours at 80° C. After cooling to room temperature, the mixture was washed with water, and the organic layer was concentrated under reduced pressure. Ethyl (1R,2R)-2-(3,4-difluorophenyl)-1-cyclopropanecarboxylate was obtained as resultant concentrate (net 49.11 g, yield: 81%).

$^1$H-NMR in (400 MHz, CDCl3)

δ 1.22-1.26 (1H, m), 1.26-1.30 (3H, t, J=7.1 Hz), 1.57-1.62 (1H, m), 1.82-1.87 (1H, m), 2.45-2.50 (1H, m), 4.14-4.20 (2H, q, J=7.1 Hz), 6.82-6.91 (2H, m), 7.02-7.09 (1H, m)

Example 3

Preparation of (1R,2R)-2-(3,4-difluorophenyl)-1-cyclopropanecarboxylic acid

Methanol (322.2 g) and 30% sodium hydroxide aqueous solution (65.5 g, 1.8 molar equivalents) were added to a solution of ethyl (1R,2R)-2-(3,4-difluorophenyl)-1-cyclopropanecarboxylate (48.2 wt % toluene solution, net 61.22 g, 270.6 mmol). The mixture was heated at 65° C. with stirring for 2 hours. The resultant mixture was concentrated under reduced pressure, then toluene and water were added to the concentrate. The mixture was acidified with 35% hydrochloric acid. The organic layer was separated and concentrated under reduced pressure. (1R,2R)-2-(3,4-difluorophenyl)-1-cyclopropanecarboxylic acid was obtained as resultant concentrate (net 52.55 g, yield: 98%).

¹H-NMR in (400 MHz, CDCl3)

δ 1.33-1.38 (1H, m), 1.64-1.69 (1H, m), 1.83-1.88 (1H, m), 2.54-2.59 (1H, m), 6.83-6.93 (2H, m), 7.04-7.10 (1H, m).

Example 4

Preparation of (1R,2R)-2-(3,4-difluorophenyl)-1-cyclopropanecarboxamide

Thionyl chloride (72.65 g, 1.21 molar equivalents) was added to the stirred toluene solution of (1R,2R)-2-(3,4-difluorophenyl)-1-cyclopropanecarboxylic acid (18 wt %, net 100.00 g, 504.62 mmol). The mixture was stirred at 35° C. for 6 hours, then concentrated under reduced pressure to give a solution of (1R,2R)-2-(3,4-difluorophenyl)-1-cyclopropanecarbonyl chloride. To a mixture of 28% ammonia aqueous solution (122.55 g, 4.00 molar equivalents), water (300.4 g) and ethyl acetate (700.2 g), the solution of (1R,2R)-2-(3,4-difluorophenyl)-1-cyclopropanecarbonyl chloride obtained above was gradually added with stirring below 10° C. The reaction mixture was allowed to stir below 10° C. for 1 hour. The mixture was neutralized with 35% hydrochloric acid, then the organic layer was separated and washed with water. The resultant solution was concentrated azeotropically under reduced pressure to give a slurry of (1R,2R)-2-(3,4-difluorophenyl)-1-cyclopropanecarboxamide. The resultant slurry was heated to obtain a clear solution, and cooled for crystallization. Hexane was added to the slurry, then the precipitates were collected by filtration and dried to give (1R,2R)-2-(3,4-difluorophenyl)-1-cyclopropanecarboxamide (net 91.12 g, Yield: 92%).

¹H-NMR in (400 MHz, CDCl3)

δ 1.21-1.27 (1H, m), 1.56-1.64 (3H, m), 2.47-2.49 (1H, m), 5.45 (1H, br), 5.63 (1H, br), 6.83-6.90 (2H, m), 7.03-7.10 (1H, m).

Example 5

Preparation of (1R,2S)-2-(3,4-difluorophenyl)-1-cyclopropanamine (1R,2R)-2-(3,4-difluorophenyl)-1-cyclopropanecarboxamide (net 9.00 g, 45.64 mmol) and 30% sodium hydroxide aqueous solution (54.77 g, 9.00 molar equivalents) were charged into a reaction vessel and the mixture was stirred. Aqueous 12% sodium hypochlorite solution (29.53 g, 2.25 mol equivalents) was added to the stirred slurry maintaining the internal temperature at 30° C. The resultant mixture was stirred at 30° C. for 14 hours, then at 40° C. for 2 hours. After completion of the reaction, isopropyl acetate was poured to the resultant mixture, then the organic layer was separated, washed with water, and concentrated under reduced pressure. (1R,2S)-2-(3,4-difluorophenyl)-1-cyclopropanamine was obtained as resultant concentrate (net 6.89 g, yield: 89%).

¹H-NMR in (400 MHz, CDCl3)

δ 0.88-0.93 (1H, m), 1.03-1.08 (1H, m), 1.70 (2H, s), 1.79-1.84 (1H, m), 2.47-2.51 (1H, m), 6.72-6.79 (2H, m), 7.00-7.02 (1H, m).

Various modifications of the invention, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, and the like) cited in the present application is incorporated herein by reference in its entirety.

What is claimed is:

1. An optically active 2-aryl cyclopropane carboxamide compound represented by general formula (17)

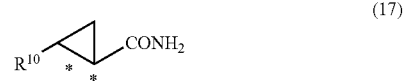

(17)

wherein, R¹⁰ is 3,4-difluorophenyl group, and * denotes an asymmetric carbon centre.

2. A compound according to claim 1 wherein the compound represented by the aforesaid formula (17) is (1R,2R)-2-aryl cyclopropane carboxamide compound.

* * * * *